(12) United States Patent
Fung et al.

(10) Patent No.: US 10,932,715 B2
(45) Date of Patent: *Mar. 2, 2021

(54) DETERMINING RESTING HEART RATE USING WEARABLE DEVICE

(71) Applicant: Microsoft Technology Licensing, LLC, Redmond, WA (US)

(72) Inventors: Han Yee Mimi Fung, Bellevue, WA (US); Haithem Albadawi, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 91 days.

This patent is subject to a terminal disclaimer.

(21) Appl. No.: 16/221,290

(22) Filed: Dec. 14, 2018

(65) Prior Publication Data

US 2019/0117150 A1  Apr. 25, 2019

Related U.S. Application Data

(63) Continuation of application No. 14/740,178, filed on Jun. 15, 2015, now Pat. No. 10,159,438.

(51) Int. Cl.
*A61B 5/00* (2006.01)
*A61B 5/024* (2006.01)
*A61B 5/01* (2006.01)
*A61B 5/0245* (2006.01)
*A61B 5/0476* (2006.01)
*A61B 5/0531* (2021.01)
*A61B 5/11* (2006.01)

(52) U.S. Cl.
CPC ........ *A61B 5/4809* (2013.01); *A61B 5/02416* (2013.01); *A61B 5/7221* (2013.01); *A61B 5/0022* (2013.01); *A61B 5/01* (2013.01); *A61B 5/0245* (2013.01); *A61B 5/02438* (2013.01); *A61B 5/0476* (2013.01); *A61B 5/0531* (2013.01); *A61B 5/1118* (2013.01); *A61B 5/6898* (2013.01); *A61B 5/7203* (2013.01)

(58) Field of Classification Search
USPC ........................................................ 600/479
See application file for complete search history.

(56) References Cited

U.S. PATENT DOCUMENTS

2014/0275852 A1* 9/2014 Hong ................... A61B 5/0002
600/301

* cited by examiner

*Primary Examiner* — Nicole F Lavert
(74) *Attorney, Agent, or Firm* — Ray Quinney & Nebeker, P.C.; Thomas M. Hardman; Steven J. Spellman

(57) ABSTRACT

A wearable device is described. The wearable device comprises: a device body configured to be secured in contact with a subject; a first sensor borne by the device body that is activatable to measure a heart rate of the subject; and control logic configured to activate the first sensor during a monitoring period during which the subject is determined to be in a sleep period.

20 Claims, 7 Drawing Sheets

DETERMINING RESTING HEART RATE USING WEARABLE DEVICE

CROSS-REFERENCE TO RELATED APPLICATION

This application is a continuation of U.S. patent application Ser. No. 14/740,178 filed on Jun. 15, 2015, which was published as U.S. Patent Application Publication No. 2016/0361011 on Dec. 15, 2016, and issued as U.S. Pat. No. 10,159,438 on Dec. 25, 2018. The aforementioned application is expressly incorporated herein by reference in its entirety.

BACKGROUND

Resting heart rate is the number of contractions of the heart that occur during a period of time, such as one minute, while the body is at rest. Resting heart rate is regarded as a significant indicator of one's level of fitness, as a strong heart can pump more blood with each contraction, thus needing to contract fewer times in a minute to provide adequate blood flow. Resting heart rate can also be an indicator of health condition, as resting heart rate tends to increase with fever. As such, many people are interested in determining their resting heart rate.

One way of measuring resting heart rate is to count contractions—such as by palpating an artery—for one minute immediately upon waking. Another way of measuring resting heart rate is to wear an electrocardiogram ("ECG") monitor during sleep as part of a medical sleep study.

SUMMARY

This summary is provided to introduce a selection of concepts in a simplified form that are further described below in the Detailed Description. This summary is not intended to identify key factors or essential features of the claimed subject matter, nor is it intended to be used to limit the scope of the claimed subject matter.

In accordance with one aspect of the present disclosure, a computer-implemented method for determining a minimum heart rate is disclosed. The method includes initializing a current minimum heart rate result and, for each of a plurality of sampling periods when a wearer of a wearable device is asleep, obtaining via the wearable device a sequence of heart rate samples for the wearer and assessing whether a threshold percentage of the heart rate samples is usable. If at least the threshold percentage of the heart rate samples is assessed to be usable, the method also includes aggregating the heart rate samples assessed to be usable. If the aggregated heart rate samples are smaller than the current minimum heart rate result, the method also includes blending the aggregated heart rate samples into the current minimum heart rate result.

The assessing, aggregating, and blending may be performed on the wearable device. Alternatively, the assessing, aggregating, and blending may be performed on a computer system distinct from the wearable device.

The heart rate samples may span a monitoring period. The sampling periods may collectively amount to a minority of the monitoring period. The method may further include activating a heart rate sensor in the wearable device during the sampling periods.

The method may further include determining that the wearer of the wearable device is asleep based upon explicit input from the wearer. Alternatively, the method may further include inferring that the wearer of the wearable device is asleep.

Aggregating the heart rate samples may include determining a value that is representative of the heart rate samples. In some embodiments, aggregating the heart rate samples may include determining at least one of a mean, a median, a mode, or a minimum of the heart rate samples.

In accordance with another aspect of the present disclosure, a computer system for determining a minimum heart rate is disclosed. The computer system includes one or more processors and memory comprising instructions that are executable by the one or more processors to perform at least some of the operations described above.

In accordance with another aspect of the present disclosure, a computer-readable medium is disclosed. The computer-readable medium has computer-executable instructions stored thereon that, when executed, cause one or more processors to perform at least some of the operations described above.

DETAILED DESCRIPTION

Figure 1:
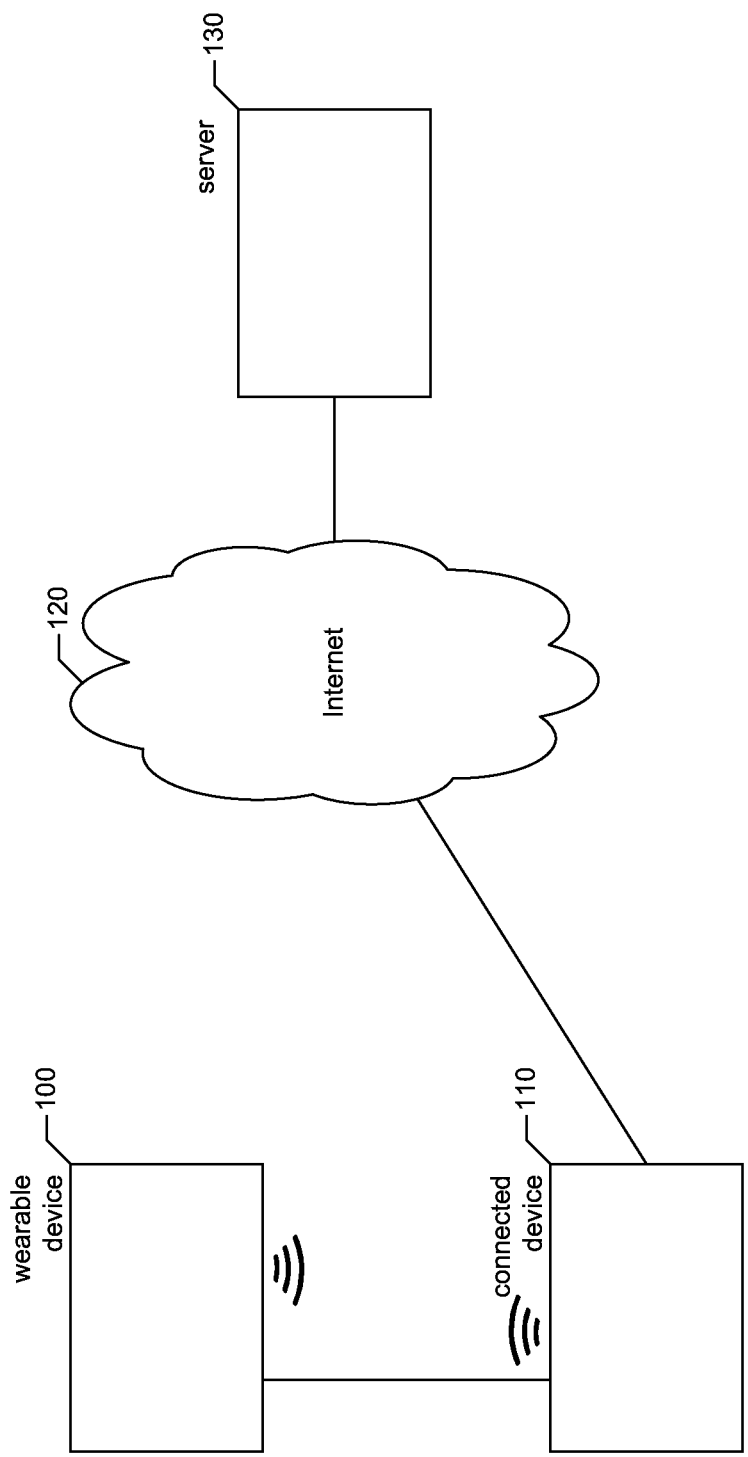
FIG. 1 is a network diagram showing an environment in which the facility operates in some embodiments.

There are a number of significant disadvantages posed by conventional approaches to measuring resting heart rate. Manually counting one's pulse on waking can be difficult for some people, as it requires: having the presence of mind on waking to take directed action; having a timepiece on hand; locating an artery; and maintaining a count while watching for expiration of a minute. Even more significantly, because the subject is awake at the time of the measurement, and must take action in order to perform the measurement, the measurement often does not reflect the subject's lowest heart rate, as wakefulness and the activity of measurement elevate the subject's heart rate relative to various points during the sleep cycle.

For this reason, the ECG measurement during a medical sleep study, at times when the subject is sleeping, is regarded by many as more accurate. Such sleep studies can be extremely expensive, however, typically costing thousands of dollars. They are also unpleasant for the subject, requiring them to enter an unfamiliar, clinical setting and attempt to sleep, typically with several kinds of sensors attached to their bodies, cameras and other instruments observing them, etc. This unpleasantness can impair the accuracy of the resting heart rate measurement, as it can interfere with the subject's ability to reach deeper stages of sleep, at which lower heart rates occur. Also, it is impractical to perform sleep studies on a recurring basis to track changes in resting heart rate over time.

In order to overcome these disadvantages of conventional approaches to measuring resting heart rate, a software and/or hardware facility is disclosed for determining a subject's resting heart rate during sleep using a wearable device worn by the subject.

In some embodiments, the wearable device worn by the subject is a type of wearable device that is, in different respects, suitable to be worn throughout the day and night. In some embodiments, the wearable device is a band that wraps around part of the subject's body, such as around the subject's wrist. In a variety of embodiments, this device performs a variety of functions in addition to determining resting heart rate, including various combinations of the following: tell time; count steps; prompt through a fitness workout routine; measure distance traveled; provide travel directions; measure a time period, such as a time period during which the subject is exercising; track sleep time and/or quality; measure light exposure, such as exposure to light in the ultraviolet frequency band; provide alarms and calendar notifications; take or view photos; send or receive email messages, text messages, instant messages, and/or voice calls; access news, weather, social network content, and/or other content; interact, such as by voice, with an automated assistant; serve electronic identification, loyalty program, and/or payment functions; etc.

In some embodiments, the device has one or more sensors usable to detect body phenomena connected to the contraction of the heart. In some embodiments, the device has an optical heart rate sensor that illuminates the subject's skin with a light source and measures—such as with a photodiode, an image sensor of another type, or a light sensor of another type—its change in light absorption resulting from the distension of arteries and arterioles in response to cardiac contractions. In some embodiments, the device includes one or more ECG sensors that measure electrical signals produced by the heart. In some embodiments, the device includes one or more bioimpedance sensors that measure changes in the impedance level of the subject's skin.

In some embodiments, the facility optimizes the energy consumed in the wearable device by collecting heart rate data only during limited periods. In some embodiments, the facility collects heart rate data for use in determining resting heart rate during a period when the subject has explicitly indicated that the subject is sleeping, or is attempting to sleep. In some embodiments, the facility collects heart rate data for use in determining resting heart rate during a period during which the facility infers that the subject is asleep. In some embodiments, the facility collects heart rate data consistently over time, and selects heart rate data for use in determining resting heart rate based on a retrospective analysis of whether the subject was asleep, and/or determines resting heart rate from this heart rate data without regard for subject sleep patterns. In some embodiments, the facility activates the device's heart rate sensors only during limited sampling periods. As examples, in various embodiments, the facility activates the device's heart rate sensors only for a one-minute or two-minute sampling period during each sampling cycle, such as a 10-minute sampling cycle.

In some embodiments, the facility uses various techniques for filtering questionable heart rate data that may correspond to sensor or other sampling errors, or may correspond to times when the subject was not sleeping, or was not sleeping soundly. In some embodiments, the facility's sample filtering techniques involves assigning each sample a quality measure. In some embodiments, the facility determines a sample's quality measure at least in part based upon whether the sample's heart rate falls within a plausible heart rate range, or within a plausible resting heart rate range. In some embodiments, the facility determines a sample's quality measure at least in part based upon various indicia, using a variety of the device's sensors, of whether the subject is resting, trying to rest, sleeping, or trying to sleep.

In some embodiments, the facility outputs the resting heart rate it determines for the subject in a variety of ways, such as by presenting it textually and/or graphically on a variety of devices, generating a chart or graph showing it over time or in comparison to other subjects' resting heart rates, storing it in the database, using it in health analysis processes, etc.

By behaving in some or all of the ways described above, the facility provides useful health information in a manner that is accurate, convenient, inexpensive, and nonintrusive, in a way that extends the battery life and/or reduces the energy storage requirements of the wearable device.

FIG. 1 is a network diagram showing an environment in which the facility operates in some embodiments. A wearable device 100 can be worn by the subject, such as around the subject's wrist. The wearable device has one or more kinds of sensors suitable for measuring the subject's heart rate. The wearable device stores heart rate measurements, or "samples," that it obtains from the subject. In various embodiments, these samples are stored and/or processed in various locations, including on the wearable device; on a connected device 110 as discussed below, and/or on a server 130 with which the connected device communicates via a network such as the Internet 120. The wearable device and the connected device are connected in one or more ways, such as via a wired or guided optical connection, via an unguided optical or radio wireless connection, etc. In various embodiments, the connected device is of a variety of different device types, including a mobile phone, a tablet, a laptop computer, a desktop computer, an automobile computer, a Wi-Fi router or access point, a cellular network transceiver, etc.

The wearable device may be implemented in any number of different form factors such as jewelry, clothing, or an assistive device. Wearable devices implemented as jewelry include wearable devices that do not substantially cover a portion of the body and have aesthetic value but may have limited functionality other than the functionality of the wearable device. Jewelry includes watches, bracelets, rings, earrings, pendants, necklaces, and the like. Wearable devices implemented as clothing include wearable devices that cover a portion of the body and share functionality with the analogous article of clothing. Examples of clothing include gloves, shoes, hats, headbands, wristbands, ankle bands, and the like. Wearable devices implemented as an assistive device include functionality that addresses a medical need of an individual. Assistive devices include glasses, hearing aids, insulin pumps, a single-purpose device that performs monitoring of the physiological data without additional functions, and the like. In some embodiments, the wearable device is said to have a portion called a "body," by which the wearable device's heart rate sensor is borne.

While various embodiments are described in terms of the environment described above, those skilled in the art will appreciate that the facility may be implemented in a variety of other environments including a single, monolithic computer system, as well as various other combinations of computer systems or similar devices connected in various ways.

Figure 2:
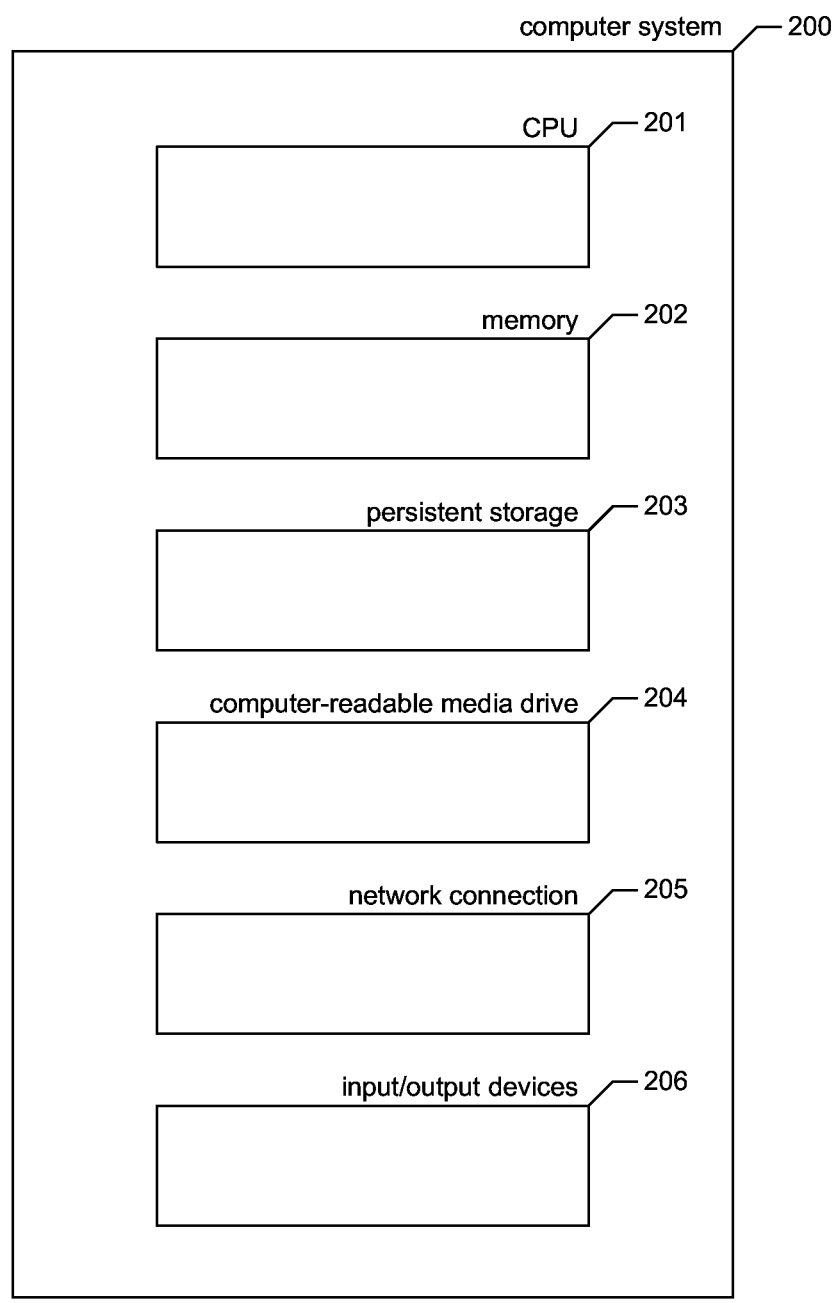
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, desktop computer systems, laptop computer systems, mobile phones, personal digital assistants, televisions, cameras, automobile computers, electronic media players, etc. In various embodiments, the computer systems and devices include zero or more of each of the following: a central processing unit ("CPU") 201 for executing computer programs; a computer memory 202 for storing programs and data while they are being used; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware; and one or more input/output devices 206, including physiological sensors of various kinds, motion sensors, microphones and speakers, orientation sensors, temperature sensors, pressure sensors, humidity sensors, a visual display, a digitizer for detecting touches between the visual display and a user's finger or other object; etc. While computer systems configured as described above are typically used to support the operation of the facility, those skilled in the art will appreciate that the facility may be implemented using devices of various types and configurations, and having various components.

Figure 3:
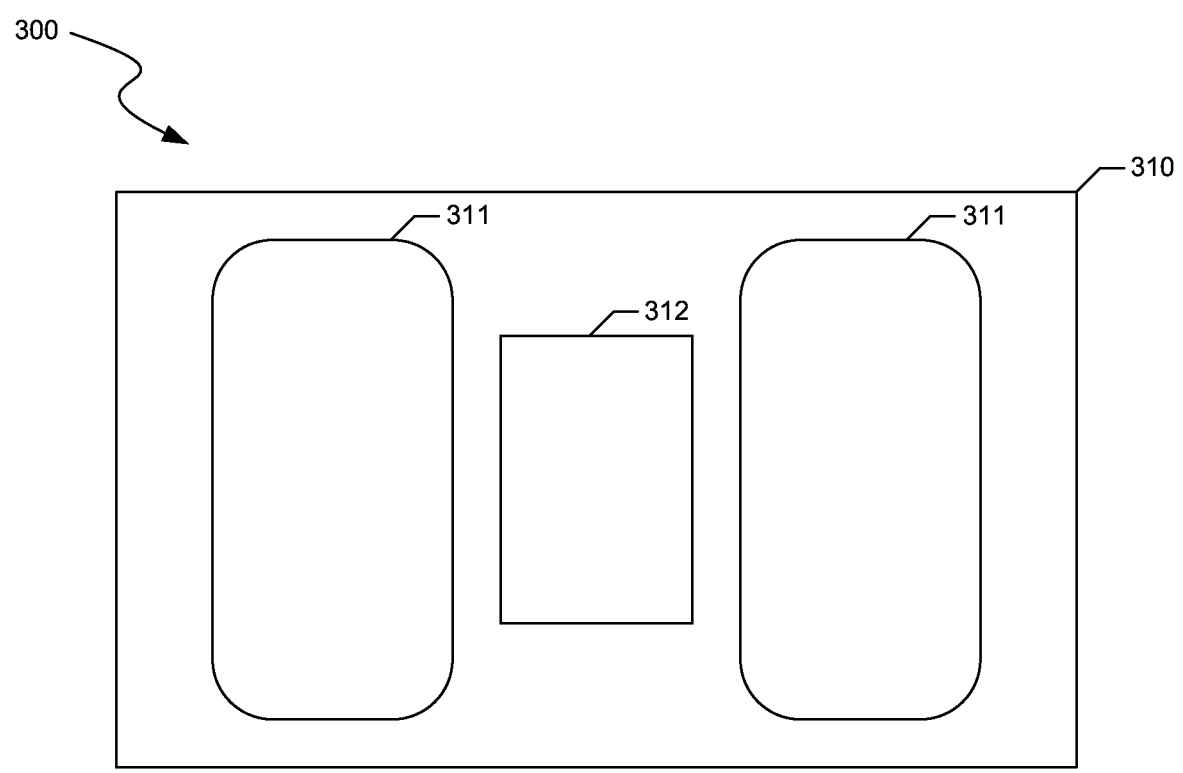
FIG. 3 is a hardware diagram showing a visual heart rate sensor used by the facility in some embodiments to capture heart rate samples.

FIG. 3 is a hardware diagram showing an optical heart rate sensor used by the facility in some embodiments to capture heart rate samples. In some embodiments, the optical heart rate sensor 310 is incorporated into a wearable device 300, and includes one or more illumination sources 311, such as light-emitting diodes, as well as a photo diode 312—or an image sensor or light sensor of another type. The optical heart rate sensor is directed toward the subject's skin, and the light sources illuminate the skin, while the sensor 312 measures changes in light absorption in the skin. In a variety of embodiments, the facility uses a variety of different sensors for capturing heart rate samples.

Figure 4:
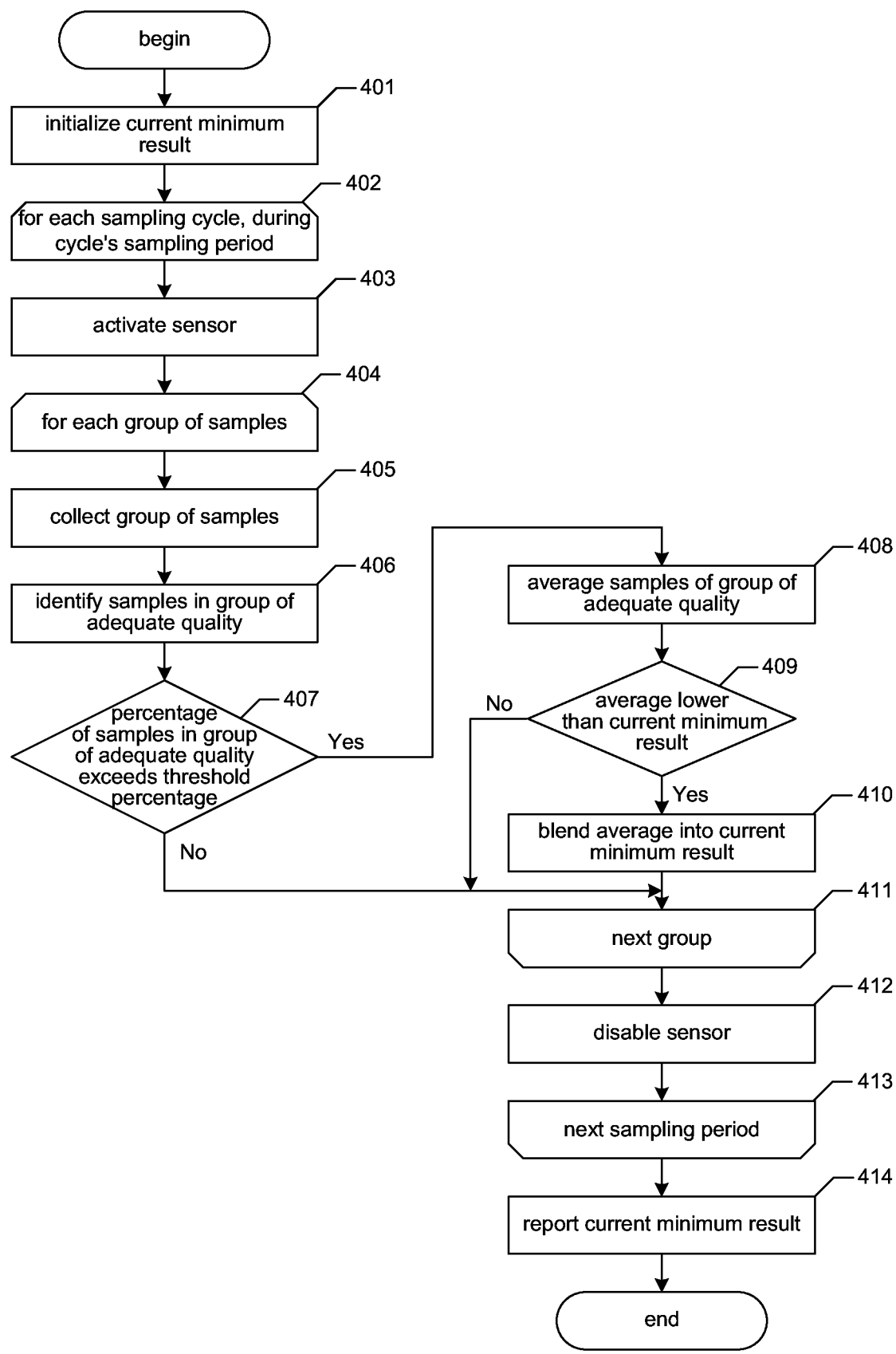
FIG. 4 is a flow diagram showing steps typically performed by the facility in order to obtain and process data to determine a subject's resting heart rate.

FIG. 4 is a flow diagram showing steps typically performed by the facility in order to obtain and process data to determine a subject's resting heart rate. In some embodiments, the facility performs the steps shown in FIG. 4 during a monitoring period, such as a monitoring period during which the subject is determined to be seeking to rest, resting, seeking to sleep, or sleeping. In some embodiments, some or all of the steps of FIG. 4 are referred to as "control logic."

In some embodiments, the facility determines the status of individual as resting or sleeping based on a manual indication from the subject whenever he or she prepares to sleep. In some embodiments, the subject activates a special-purpose input device of the wearable device, such as a physical button, to provide this manual indication. In some embodiments, the subject uses a general-purpose input device for this purpose, such as by activating a visual user input tile on a touch screen, or by speaking a verbal command. In some embodiments, the end of resting is also indicated manually when the subject wakes. Resting or sleeping status may be detected automatically by the wearable device, or retrospectively by another device. In various embodiments, the wearable device uses any number of different sensors to detect that the subject is resting or sleeping. For example, in some embodiments, a motion sensor, such as an accelerometer or gyroscope, in the wearable electronic device detects motion of the individual, and the facility uses an absence of motion to infer that the individual is resting. In various embodiments, the facility also uses measurement of physiological features such as skin temperature, heart rate, and/or respiration rate to infer a state of rest or sleep. Because skin temperature, heart rate, and respiration rate all decrease during normal sleep, in some embodiments, the facility uses these measures to identify the individual's sleep and wake cycle. In some embodiments, the facility uses a wearable device that detects brain waves such as an electroencephalogram (EEG) to determine that the subject is sleeping. In some embodiments, the facility infers the status of the individual as resting or sleeping based on time; for example, in some embodiments, the facility assumes that the subject is resting or asleep between the times of 1 AM and 5 AM. In some embodiments, some or all of these techniques for determining whether the subject is in a sleep period are referred to as "analysis logic."

In step 401, the facility initializes a current minimum result value in which the facility stores the lowest heart rate thus far attributed to the subject during analysis session. In steps 402-413, the facility loops through each sampling cycle, such as a sampling cycle 10 minutes long. Steps 403-412 describe steps performed during the current sampling cycle's sampling period, such as a sampling period two minutes long, or a sampling period one minute long. In step 403, the facility activates the device's heart rate sensor. The facility repeats steps 404-411 for each group of samples collected by the facility during the current cycle's sampling period. In step 405, the facility collects a group of samples. In some embodiments, a group is defined as a certain number of samples. In some embodiments, samples are collected at a fixed frequency, such as once per second. In some embodiments, in order to collect a group of samples, the facility monitors the samples being outputted by the heart rate sensor, and waits until a sample is received that is determined to be of adequate quality. In some embodiments, the facility determines a numerical quality measure for each sample that it uses to assess whether each sample is of adequate quality for use. Some factors used in determining a sample's measure of quality include the extent to which a sample's heart rate is within a reasonable range, such as between 35 beats per minute and 85 beats per minute; the degree to which various sensors indicate that the subject is asleep, such as motion sensors indicating that the only motions the device is undergoing are consistent with the subject being asleep; whether sounds received by the microphone are consistent with the user being asleep; whether device orientation determined by orientation sensors are consistent with the user being asleep; whether sensors reflecting the positioning of the device and its heart rate sensors reflect that these are correctly positioned relative to the subject's body for capturing accurate samples; whether the level of light reported by outward-facing light sensors is consistent with a sleeping environment; etc. In some embodiments, in order to collect a group of samples, the facility group collects a group of 20 contiguous samples that begin with the next sample having an adequate quality measure.

In step 406, the facility identifies samples in the collected in step 405 that are of adequate quality, such as those having a quality measure that exceeds a quality level threshold. In step 407, if the percentage of samples in the group determined in step 406 to be of adequate quality exceeds a threshold percentage, then the facility continues in step 408, else the facility continues in step 411. In step 408, the facility aggregates the samples of the group determined to be of adequate quality in step 406, such as by computing the mean, median, mode, etc. of these samples. In step 409, if the aggregated value determined in step 408 is lower than the current minimum result, then the facility continues in step 410, else the facility continues in step 411. In step 410, the facility blends the aggregated value determined in step 408 into the current minimum result. Where the current minimum result is in its initialized state from step 401, the facility simply substitutes the aggregate value from step 408 for this initialized state. Otherwise, the facility computes a weighted average of the current minimum result and the aggregated value determined in step 408, such as by adding 40% of the aggregated value to 60% of the current minimum result.

In step 411, if the sampling period has not ended, the facility continues in step 404 to collect and process the next group of samples. In step 412, on the expiration of the current sampling period, the facility disables the heart rate sensor in the device. In step 413, the facility continues in step 402 to reactivate the sensor at the beginning of the next sampling cycle period. In step 414, such as at the end of the night, or at an arbitrary time, or at a time when various sensors reflect that a sleeping period has ended, or at a time when the user explicitly indicates that sleep has ended, the facility reports the current value of the current minimum result as modified in step 410. After step 414, these steps conclude.

Those skilled in the art will appreciate that the steps shown in FIG. 4 and in each of the flow diagrams discussed below may be altered in a variety of ways. For example, the order of the steps may be rearranged; some steps may be performed in parallel; shown steps may be omitted, or other steps may be included; a shown step may divided into substeps, or multiple shown steps may be combined into a single step, etc.

Figure 5:
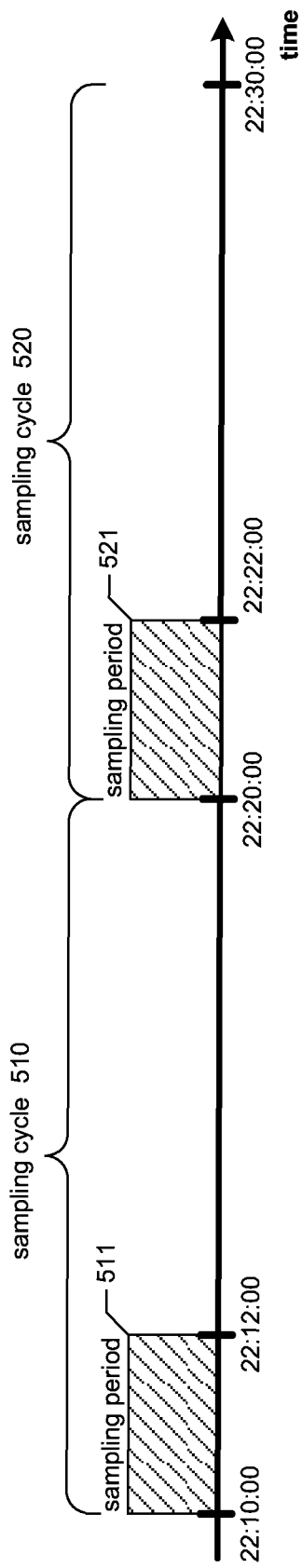
FIG. 5 is a timing diagram showing the relationship of sampling periods to sampling cycles.

FIG. 5 is a timing diagram showing the relationship of sampling periods to sampling cycles. It can be seen that, in FIG. 5, each of sampling cycles 510 and 520 is 10 minutes long. For example, sampling cycle 510 lasts from 22:10:00 to 22:20:00. Each of sampling periods 511 and 521 is the first two minutes of the sampling cycle that contains it. For example, sampling period 511 lasts between 22:10:00 and 22:12:00.

Figure 6:
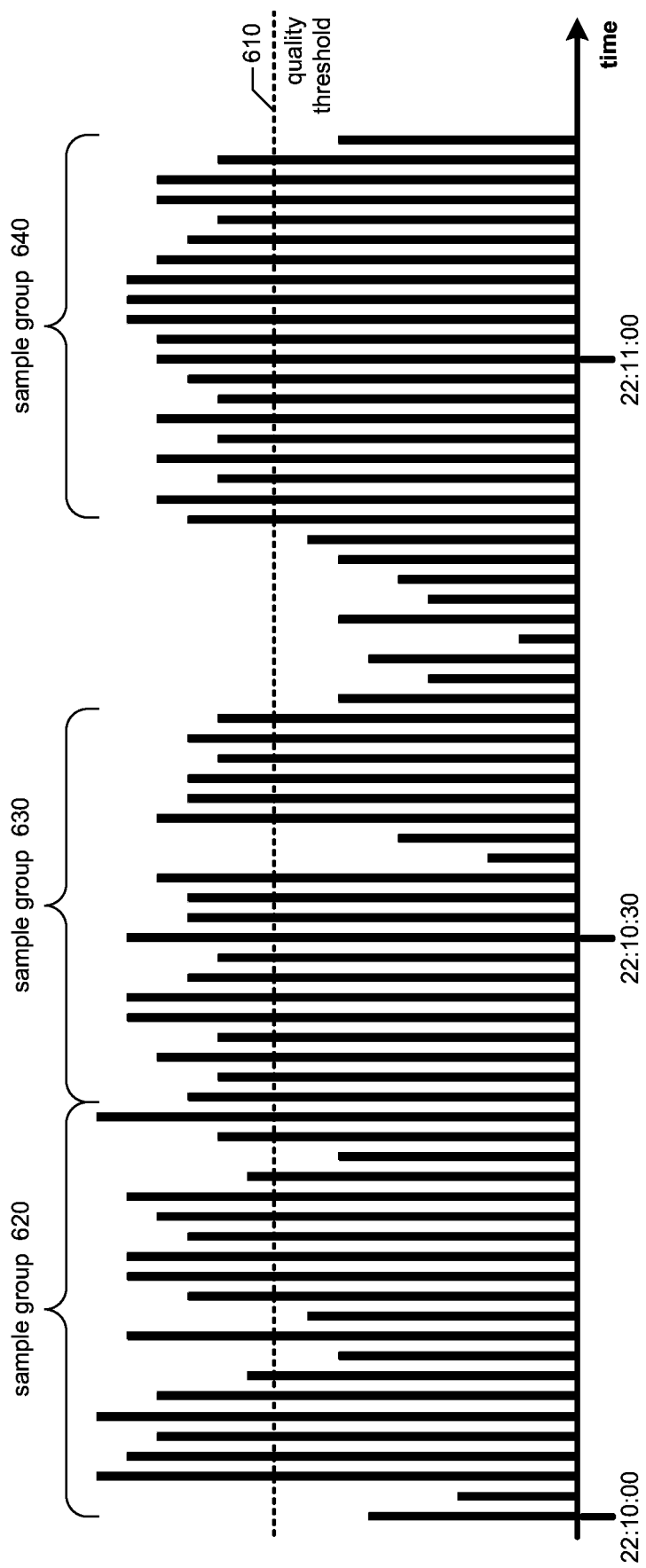
FIG. 6 is a timing diagram showing a set of samples collected by the facility during sampling period 511 shown in FIG. 5.

FIG. 6 is a timing diagram showing a set of samples collected by the facility during sampling period 511 shown in FIG. 5. Each sample collected by the facility is represented by a vertical line at a different point on the timeline whose height reflects the sample's quality measure. These samples are reflected in numerical form in Table 1 below. This table shows, for each of the samples: the time at which the sample was collected; the quality measure attributed to the sample; and the heart rate measured in the sample. For example, the first row of Table 1 indicates that, at time 22:10:01, a heart rate of 15 beats per minute was measured, and attributed a sample quality value of 7. The heart rates shown in Table 1 are for illustrative purposes only, and do not necessarily correspond to a particular subject having a particular fitness or health level.

TABLE 1

| time | sample heart rate | sample quality |
|---|---|---|
| 22:10:01 | 15 | 7 |
| 22:10:02 | 8 | 4 |
| 22:10:03 | 48 | 16 |
| 22:10:04 | 51 | 15 |
| 22:10:05 | 50 | 14 |
| 22:10:06 | 47 | 16 |
| 22:10:07 | 46 | 14 |
| 22:10:08 | 47 | 11 |
| 22:10:09 | 46 | 8 |
| 22:10:10 | 48 | 15 |
| 22:10:11 | 46 | 9 |
| 22:10:12 | 48 | 13 |
| 22:10:13 | 47 | 15 |
| 22:10:14 | 47 | 15 |
| 22:10:15 | 47 | 13 |
| 22:10:16 | 44 | 14 |
| 22:10:17 | 49 | 15 |
| 22:10:18 | 48 | 11 |
| 22:10:19 | 12 | 8 |
| 22:10:20 | 48 | 12 |
| 22:10:21 | 47 | 16 |
| 22:10:22 | 48 | 13 |
| 22:10:23 | 49 | 12 |
| 22:10:24 | 50 | 14 |
| 22:10:25 | 51 | 12 |
| 22:10:26 | 50 | 15 |
| 22:10:27 | 51 | 15 |
| 22:10:28 | 49 | 13 |
| 22:10:29 | 47 | 12 |
| 22:10:30 | 49 | 15 |
| 22:10:31 | 49 | 13 |
| 22:10:32 | 51 | 13 |
| 22:10:33 | 53 | 14 |
| 22:10:34 | 58 | 3 |
| 22:10:35 | 59 | 6 |
| 22:10:36 | 49 | 14 |
| 22:10:37 | 50 | 13 |
| 22:10:38 | 49 | 13 |
| 22:10:39 | 48 | 12 |
| 22:10:40 | 47 | 13 |
| 22:10:41 | 49 | 12 |
| 22:10:42 | 88 | 8 |
| 22:10:43 | 92 | 5 |
| 22:10:44 | 103 | 7 |
| 22:10:45 | 155 | 2 |
| 22:10:46 | 132 | 8 |
| 22:10:47 | 119 | 5 |
| 22:10:48 | 115 | 6 |
| 22:10:49 | 100 | 8 |
| 22:10:50 | 96 | 9 |
| 22:10:51 | 47 | 13 |
| 22:10:52 | 45 | 14 |
| 22:10:53 | 46 | 12 |
| 22:10:54 | 45 | 14 |
| 22:10:55 | 46 | 12 |
| 22:10:56 | 45 | 14 |
| 22:10:57 | 45 | 12 |
| 22:10:58 | 47 | 13 |
| 22:10:59 | 44 | 14 |
| 22:11:00 | 45 | 14 |
| 22:11:01 | 45 | 15 |
| 22:11:02 | 46 | 15 |
| 22:11:03 | 45 | 15 |
| 22:11:04 | 45 | 14 |
| 22:11:05 | 44 | 13 |
| 22:11:06 | 44 | 12 |
| 22:11:07 | 45 | 14 |
| 22:11:08 | 45 | 14 |
| 22:11:09 | 46 | 12 |
| 22:11:10 | 8 | 8 |

Beginning at time 22:10:00 when sampling period 511 begins, the facility observes samples until it reaches the next sample whose quality measure exceeds a quality threshold 610. In Table 1, the quality threshold corresponds to the quality value 10. As can be seen in both FIG. 6 and Table 1, the first such sample occurs at time 22:10:03, which, unlike the samples at times 22:10:01 and 22:10:02, has a quality measure that exceeds 10. Sample group 620 then includes the sample at 22:10:03, as well as the succeeding 19 samples. These are shown below in Table 2.

TABLE 2

| time | sample heart rate | sample quality |
|---|---|---|
| 22:10:03 | 48 | 16 |
| 22:10:04 | 51 | 15 |
| 22:10:05 | 50 | 14 |
| 22:10:06 | 47 | 16 |
| 22:10:07 | 46 | 14 |
| 22:10:08 | 47 | 11 |
| 22:10:09 | 46 | 8 |
| 22:10:10 | 48 | 15 |
| 22:10:11 | 46 | 9 |
| 22:10:12 | 48 | 13 |
| 22:10:13 | 47 | 15 |
| 22:10:14 | 47 | 15 |
| 22:10:15 | 47 | 13 |
| 22:10:16 | 44 | 14 |
| 22:10:17 | 49 | 15 |
| 22:10:18 | 48 | 11 |
| 22:10:19 | 12 | 8 |
| 22:10:20 | 48 | 12 |
| 22:10:21 | 47 | 16 |
| 22:10:22 | 48 | 13 |

After collecting sample group 620, the facility identifies the samples in the sample group that are of an adequate quality level, such as those that exceed the quality threshold of 10.

Table 3 below shows the samples of sample group 620 whose quality the facility determines to be adequate. By comparing Table 3 to Table 2, it can be seen that samples from the following times have been removed as not being of adequate quality: 22:10:09, 22:10:11, and 22:10:19.

TABLE 3

| time | sample heart rate | sample quality |
|---|---|---|
| 22:10:03 | 48 | 16 |
| 22:10:04 | 51 | 15 |
| 22:10:05 | 50 | 14 |
| 22:10:06 | 47 | 16 |
| 22:10:07 | 46 | 14 |
| 22:10:08 | 47 | 11 |
| 22:10:10 | 48 | 15 |
| 22:10:12 | 48 | 13 |
| 22:10:13 | 47 | 15 |
| 22:10:14 | 47 | 15 |
| 22:10:15 | 47 | 13 |
| 22:10:16 | 44 | 14 |
| 22:10:17 | 49 | 15 |
| 22:10:18 | 48 | 11 |
| 22:10:20 | 48 | 12 |
| 22:10:21 | 47 | 16 |
| 22:10:22 | 48 | 13 | mean: 47.6
current minimum result: 47.6

In various embodiments, the facility applies various aggregation functions to the remaining sample heart rates, such as mean, median, mode, minimum, etc. In the example, the facility computes the mean of the remaining sample heart rates as a means of filtering out aberrantly low samples that would be given greater credence by the minimum aggregation function, arriving at a mean of 47.6. As the sample group 620 is the first sample group determined in this resting heart rate determination period, the facility simply copies this mean value of 47.6 to the current minimum result.

Table 4 below shows the samples of sample group 630 that the facility deems to be of adequate quality. Table 4 further shows a mean heart rate of 49.5 beats per minute. Because this mean value of 49.5 is larger than the current minimum result of 47.6, the facility does not change the current minimum result in response to sample group 630.

TABLE 4

| time | sample heart rate | sample quality |
|---|---|---|
| 22:10:23 | 49 | 12 |
| 22:10:24 | 50 | 14 |
| 22:10:25 | 51 | 12 |
| 22:10:26 | 50 | 15 |
| 22:10:27 | 51 | 15 |
| 22:10:28 | 49 | 13 |
| 22:10:29 | 47 | 12 |
| 22:10:30 | 49 | 15 |
| 22:10:31 | 49 | 13 |
| 22:10:32 | 51 | 13 |
| 22:10:33 | 53 | 14 |
| 22:10:36 | 49 | 14 |
| 22:10:37 | 50 | 13 |
| 22:10:38 | 49 | 13 |
| 22:10:39 | 48 | 12 |
| 22:10:40 | 47 | 13 |
| 22:10:41 | 49 | 12 | mean: 49.5
current minimum result: 47.6

Table 5 below shows the samples of sample group 640 of adequate quality. These have a mean heart rate of 45.3 beats per minute. Because the mean of 45.3 beats per minute of sample group 640 is less than the current minimum result of 47.6, the facility blends the current mean of 45.3 into the current minimum result. In general, the facility weights the mean of the current sample group against the current minimum result in a consistent way to moderate the speed with which the current minimum result adapts toward the current sample group mean. In some embodiments, the facility weights the current minimum result higher than the current sample group mean, such as at 60% vs. 40%. In the example, the facility obtains a new current minimum result of 47.6 to reach a new current minimum result of 46.7 by weighting the mean for sample group 640 at 40% and the prior current minimum result at 60%.

TABLE 5

| time | sample heart rate | sample quality |
|---|---|---|
| 22:10:51 | 47 | 13 |
| 22:10:52 | 45 | 14 |
| 22:10:53 | 46 | 12 |
| 22:10:54 | 45 | 14 |
| 22:10:55 | 46 | 12 |
| 22:10:56 | 45 | 14 |
| 22:10:57 | 45 | 12 |
| 22:10:58 | 47 | 13 |
| 22:10:59 | 44 | 14 |
| 22:11:00 | 45 | 14 |
| 22:11:01 | 45 | 15 |
| 22:11:02 | 46 | 15 |
| 22:11:03 | 45 | 15 |
| 22:11:04 | 45 | 14 |
| 22:11:05 | 44 | 13 |
| 22:11:06 | 44 | 12 |
| 22:11:07 | 45 | 14 |
| 22:11:08 | 45 | 14 |
| 22:11:09 | 46 | 12 | mean: 45.3
current minimum result: 46.7

Figure 7:
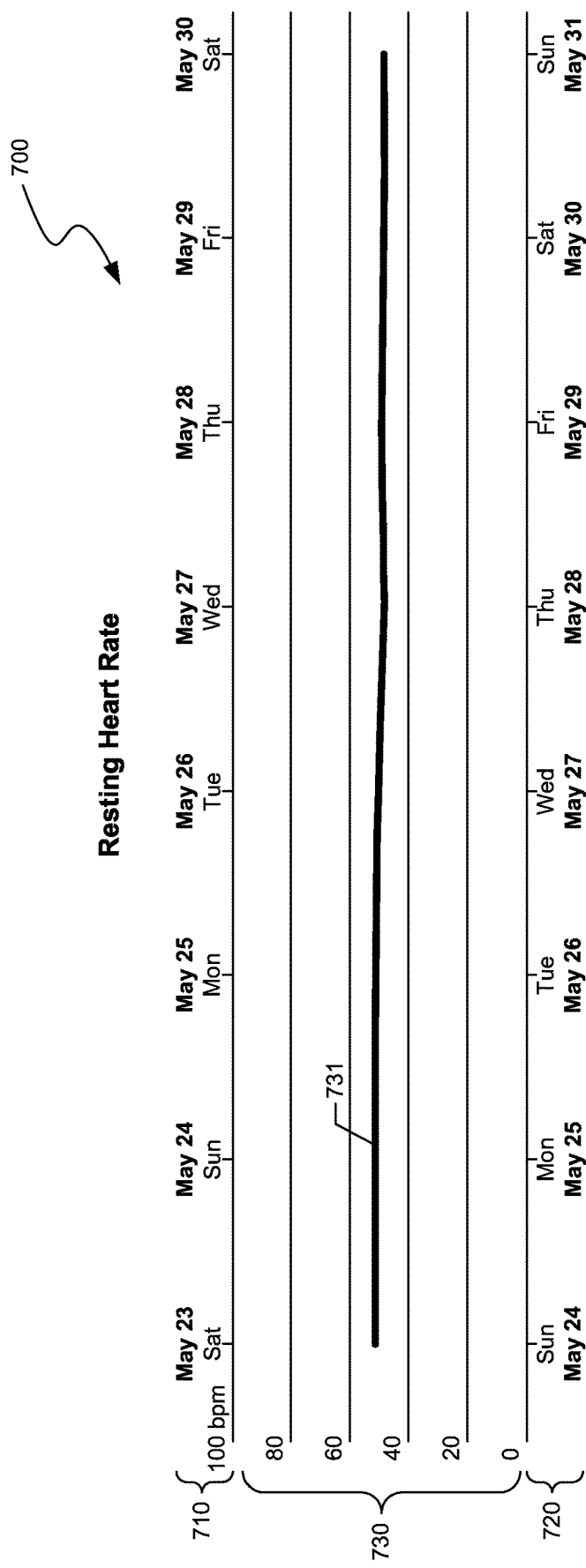
FIG. 7 is a display diagram showing a sample display that conveys a resting heart rate determined by the facility.

FIG. 7 is a display diagram showing a sample display that conveys a resting heart rate determined by the facility. In a variety of embodiments, the facility causes this display to be presented via a variety of display devices. It can be seen that the display 700 includes a timeline, along which the subject's minimum resting heart rate 731 is plotted. The timeline contains two time index components: a time index component 710 showing the day and date when the sleep period began, and a time index component 720 showing the day and date when the sleep period ended. The display also includes a scale 730 that reflects the minimum resting heart beat that was determined by the facility during each of the sleep periods. In various embodiments, the display has various other characteristics, such as the ability for a user to hover a mouse cursor over a spot on plot 731, or touch such a spot with their finger, to have displayed a numerical value of the heart minimum resting heart beat determined on that day.

In some embodiments, the facility stores the resting heart rate it determines for a subject in a table, such as a table made up of entries each containing a determined resting heart rate, and an indication of when the samples were collected that were used in the determination.

In some embodiments, the facility provides a wearable device. The wearable device comprises: a device body configured to be secured in contact with a subject; a first sensor borne by the device body that is activatable to measure a heart rate of the subject; and control logic configured to activate the first sensor during a monitoring period during which the subject is determined to be in a sleep period.

In some embodiments, the facility provides a computer-readable medium having contents configured to cause a computing system to: initialize a current minimum heartbeat result; during a period when a wearer of a wearable device is determined to be in a sleep period: for each of a plurality of sampling periods: obtain via the device a sequence of heart rate samples for the wearer; for each of the samples, assess whether the sample is usable; if at least the threshold percentage of the samples are assessed to be usable: aggregate the samples assessed to be usable; and if the aggregated samples are smaller than the current minimum heartbeat result, blend the aggregated samples into the current minimum heartbeat result.

In some embodiments, the facility provides a method in a computing system, comprising: initializing a current minimum heartbeat result; during a period when a wearer of a wearable device is determined to be in a sleep period: for each of a plurality of sampling periods: obtaining via the device a sequence of heart rate samples for the wearer; for each of the samples, assessing whether the sample is usable; if at least the threshold percentage of the samples are assessed to be usable: aggregating the samples assessed to be usable; and if the aggregated samples are smaller than the current minimum heartbeat result, blending the aggregated samples into the current minimum heartbeat result.

In some embodiments, the facility provides a computer-readable medium storing a resting heart rate data structure for a subject. The data structure comprises: a plurality of entries, each entry corresponding to a different sleep period of the subject, each entry comprising: a quantitative indication of a resting heart rate for the subject, the indication having been generated from heart rate samples captured from the subject by a wearable device during the sleep period.

It will be appreciated by those skilled in the art that the above-described facility may be straightforwardly adapted or extended in various ways. While the foregoing description makes reference to particular embodiments, the scope of the invention is defined solely by the claims that follow and the elements recited therein.

What is claimed is:

1. A computer-implemented method for determining a minimum heart rate, comprising:
   initializing a current minimum heart rate result; and
   for each of a plurality of sampling periods when a wearer of a wearable device is asleep:
      obtaining via the wearable device a sequence of heart rate samples for the wearer;
      assessing whether a threshold percentage of the heart rate samples is usable; and
      if at least the threshold percentage of the heart rate samples is assessed to be usable:
         aggregating the heart rate samples assessed to be usable, wherein aggregating the heart rate samples comprises determining a value that is representative of the heart rate samples; and
         if the aggregated heart rate samples are smaller than the current minimum heart rate result, blending the aggregated heart rate samples into the current minimum heart rate result.

2. The method of claim 1, wherein the assessing, aggregating, and blending are performed on the wearable device.

3. The method of claim 1, wherein the assessing, aggregating, and blending are performed on a computer system distinct from the wearable device.

4. The method of claim 1, wherein:
   the heart rate samples span a monitoring period;
   the sampling periods collectively amount to a minority of the monitoring period; and
   the method further comprises activating a heart rate sensor in the wearable device during the sampling periods.

5. The method of claim 1, further comprising determining that the wearer of the wearable device is asleep based upon explicit input from the wearer.

6. The method of claim 1, further comprising inferring that the wearer of the wearable device is asleep.

7. The method of claim 1, wherein aggregating the heart rate samples comprises determining at least one of a mean, a median, a mode, or a minimum of the heart rate samples.

8. A computer system for determining a minimum heart rate, comprising:
   one or more processors; and
   memory comprising instructions that are executable by the one or more processors to:
      initialize a current minimum heart rate result; and
      for each of a plurality of sampling periods when a wearer of a wearable device is asleep:
         obtain via the wearable device a sequence of heart rate samples for the wearer;
         assess whether a threshold percentage of the heart rate samples is usable; and
         if at least the threshold percentage of the heart rate samples is assessed to be usable:
            aggregate the heart rate samples assessed to be usable, wherein aggregating the heart rate samples comprises determining a value that is representative of the heart rate samples; and
            if the aggregated heart rate samples are smaller than the current minimum heart rate result, blend the aggregated heart rate samples into the current minimum heart rate result.

9. The computer system of claim 8, wherein the computer system comprises the wearable device.

10. The computer system of claim 8, wherein the computer system is distinct from the wearable device.

11. The computer system of claim 8, wherein:
the heart rate samples span a monitoring period;
the sampling periods collectively amount to a minority of the monitoring period; and
the instructions are additionally executable by the one or more processors to activate a heart rate sensor in the wearable device during the sampling periods.

12. The computer system of claim 8, wherein the instructions are additionally executable by the one or more processors to determine that the wearer of the wearable device is asleep based upon explicit input from the wearer.

13. The computer system of claim 8, wherein the instructions are additionally executable by the one or more processors to infer that the wearer of the wearable device is asleep.

14. The computer system of claim 8, wherein the instructions that are executable by the one or more processors to aggregate the heart rate samples comprise instructions that are executable by the one or more processors to determine at least one of a mean, a median, a mode, or a minimum of the heart rate samples.

15. A computer-readable medium having computer-executable instructions stored thereon that, when executed, cause one or more processors to:
initialize a current minimum heart rate result; and
for each of a plurality of sampling periods when a wearer of a wearable device is asleep:
obtain via the wearable device a sequence of heart rate samples for the wearer;
assess whether a threshold percentage of the heart rate samples is usable; and
if at least the threshold percentage of the heart rate samples is assessed to be usable:
aggregate the heart rate samples assessed to be usable, wherein aggregating the heart rate samples comprises determining a value that is representative of the heart rate samples; and
if the aggregated heart rate samples are smaller than the current minimum heart rate result, blend the aggregated heart rate samples into the current minimum heart rate result.

16. The computer-readable medium of claim 15, wherein the wearable device assesses whether the threshold percentage of the heart rate samples is usable, aggregates the heart rate samples assessed to be usable, and blends the aggregated heart rate samples into the current minimum heart rate result.

17. The computer-readable medium of claim 15, wherein a computer system distinct from the wearable device assesses whether the threshold percentage of the heart rate samples is usable, aggregates the heart rate samples assessed to be usable, and blends the aggregated heart rate samples into the current minimum heart rate result.

18. The computer-readable medium of claim 15, wherein:
the heart rate samples span a monitoring period;
the sampling periods collectively amount to a minority of the monitoring period; and
the computer-executable instructions additionally cause the one or more processors to activate a heart rate sensor in the wearable device during the sampling periods.

19. The computer-readable medium of claim 15, wherein the computer-executable instructions additionally cause the one or more processors to determine that the wearer of the wearable device is asleep based upon explicit input from the wearer.

20. The computer-readable medium of claim 15, wherein the computer-executable instructions additionally cause the one or more processors to infer that the wearer of the wearable device is asleep.

* * * * *